(12) United States Patent
Wiener et al.

(10) Patent No.: US 8,775,198 B2
(45) Date of Patent: Jul. 8, 2014

(54) SYSTEM AND METHOD FOR PERFORMING A REMOTE VERIFICATION OF A PHARMACY FILL UTILIZING AN IMAGE TO IMAGE COMPARISON

(75) Inventors: Adam S. Wiener, Lake Zurich, IL (US); Rong Huang, Buffalo Grove, IL (US)

(73) Assignee: Walgreen Co., Deerfield, IL (US)

( * ) Notice: Subject to any disclaimer, the term of this patent is extended or adjusted under 35 U.S.C. 154(b) by 1390 days.

(21) Appl. No.: 11/881,365

(22) Filed: Jul. 25, 2007

(65) Prior Publication Data

US 2009/0030722 A1    Jan. 29, 2009

(51) Int. Cl.
*G06Q 10/00*    (2012.01)
*G06Q 50/00*    (2012.01)

(52) U.S. Cl.
USPC .............................................................. 705/2

(58) Field of Classification Search
CPC ............................... G06Q 50/22; G06F 19/324
USPC ....................................................... 705/2, 3
See application file for complete search history.

(56) References Cited

U.S. PATENT DOCUMENTS

| | | |
|---|---|---|
| 4,457,772 A | 7/1984 | Haynes et al. |
| 4,852,001 A | 7/1989 | Tsushima et al. |
| 5,053,970 A | 10/1991 | Kurihara et al. |
| 5,072,383 A | 12/1991 | Brimm et al. |
| 5,260,868 A | 11/1993 | Gupta et al. |
| 5,289,370 A | 2/1994 | Lirov |
| 5,299,121 A | 3/1994 | Brill et al. |
| 5,337,919 A | 8/1994 | Spaulding et al. |
| 5,548,518 A | 8/1996 | Dietrich et al. |
| 5,559,710 A | 9/1996 | Shahraray et al. |
| 5,597,995 A | 1/1997 | Williams et al. |
| 5,615,121 A | 3/1997 | Babayev et al. |
| 5,619,991 A | 4/1997 | Sloane |
| 5,630,070 A | 5/1997 | Dietrich et al. |
| 5,737,539 A | 4/1998 | Edelson et al. |
| 5,737,728 A | 4/1998 | Sisley et al. |
| 5,748,907 A | 5/1998 | Crane |
| 5,758,095 A | 5/1998 | Albaum et al. |
| 5,765,139 A | 6/1998 | Bondy |
| 5,790,785 A | 8/1998 | Klug et al. |
| 5,797,515 A | 8/1998 | Liff et al. |

(Continued)

FOREIGN PATENT DOCUMENTS

| | | |
|---|---|---|
| EP | 0 921 488 A1 | 6/1999 |
| JP | 361217880 | 9/1986 |
| WO | WO-96/13790 A1 | 5/1996 |
| WO | WO-01/08393 A1 | 2/2001 |

OTHER PUBLICATIONS

"The Virtual Pharmacist," *Rural Electric*, vol. 60, No. 6, Mar. 2002, p. 20.
Anonymous, "CVS, Merck-Medco in E-commerce Alliance," Chain Drug Review, 21(18):2 (1999).
Anonymous, "Name Change Reflects CVS' Commitment to E-commerce," Chain Drug Review, 21(15):2 (1999).
Colchamiro, "Independents Look to Go Online," American Druggist, Sep. 1999, pp. 1-3.

(Continued)

*Primary Examiner* — John Pauls
*Assistant Examiner* — Trang Nguyen
(74) *Attorney, Agent, or Firm* — Francis C. Kowalik; Marshall, Gerstein & Borun LLP; Randall G. Rueth (57) ABSTRACT

The method and system provides image data of a prepared pharmacy product for review by a pharmacist located away from the prepared pharmacy product. The method and system enables the verification process to be ported to locations in which resources may be more efficiently utilized.

12 Claims, 11 Drawing Sheets

(56) References Cited

U.S. PATENT DOCUMENTS

| | | | |
|---|---|---|---|
| 5,801,755 A | 9/1998 | Echerer | |
| 5,826,236 A | 10/1998 | Narimatsu et al. | |
| 5,826,252 A | 10/1998 | Wolters, Jr. et al. | |
| 5,845,255 A | 12/1998 | Mayaud | |
| 5,852,259 A | 12/1998 | Yanase et al. | |
| 5,907,493 A | 5/1999 | Boyer et al. | |
| 5,911,687 A | 6/1999 | Sato et al. | |
| 5,915,240 A | 6/1999 | Karpf | |
| 5,924,074 A | 7/1999 | Evans | |
| 5,946,883 A | 9/1999 | Yuyama et al. | |
| 5,954,640 A | 9/1999 | Szabo | |
| 5,963,911 A | 10/1999 | Walker et al. | |
| 5,970,462 A | 10/1999 | Reichert | |
| 5,987,519 A | 11/1999 | Peifer et al. | |
| 6,025,984 A * | 2/2000 | Borkowski | 361/679.09 |
| 6,067,524 A | 5/2000 | Byerly et al. | |
| 6,078,912 A | 6/2000 | Buerger et al. | |
| 6,112,182 A | 8/2000 | Akers et al. | |
| 6,202,080 B1 | 3/2001 | Lu et al. | |
| 6,202,923 B1 | 3/2001 | Boyer et al. | |
| 6,208,973 B1 | 3/2001 | Boyer et al. | |
| 6,256,550 B1 | 7/2001 | Wu et al. | |
| 6,266,655 B1 | 7/2001 | Kalyan | |
| 6,294,999 B1 | 9/2001 | Yarin et al. | |
| 6,311,163 B1 | 10/2001 | Sheehan et al. | |
| 6,330,491 B1 | 12/2001 | Lion | |
| 6,347,329 B1 | 2/2002 | Evans | |
| 6,364,517 B1 | 4/2002 | Yuyama et al. | |
| 6,370,841 B1 | 4/2002 | Chudy et al. | |
| 6,381,577 B1 | 4/2002 | Brown | |
| 6,397,190 B1 | 5/2002 | Goetz | |
| 6,421,650 B1 | 7/2002 | Goetz et al. | |
| 6,438,451 B1 | 8/2002 | Lion | |
| 6,463,417 B1 | 10/2002 | Schoenberg | |
| 6,464,142 B1 | 10/2002 | Denenberg et al. | |
| 6,477,442 B1 | 11/2002 | Valerino, Sr. | |
| 6,493,427 B1 | 12/2002 | Kobylevsky et al. | |
| 6,496,427 B2 | 12/2002 | Kojima et al. | |
| 6,523,009 B1 | 2/2003 | Wilkins | |
| 6,535,637 B1 * | 3/2003 | Wootton et al. | 382/190 |
| 6,539,281 B2 | 3/2003 | Wan et al. | |
| 6,564,121 B1 | 5/2003 | Wallace et al. | |
| 6,625,952 B1 | 9/2003 | Chudy et al. | |
| 6,665,740 B1 | 12/2003 | Mason, Jr. et al. | |
| 6,711,460 B1 | 3/2004 | Reese | |
| 6,735,497 B2 | 5/2004 | Wallace et al. | |
| 6,741,724 B1 | 5/2004 | Bruce et al. | |
| 6,760,749 B1 | 7/2004 | Dunlap et al. | |
| 6,771,369 B2 | 8/2004 | Rzasa et al. | |
| 6,804,654 B2 | 10/2004 | Kobylevsky et al. | |
| 6,874,684 B1 | 4/2005 | Denenberg et al. | |
| 6,947,900 B2 | 9/2005 | Giordano, III et al. | |
| 7,006,214 B2 * | 2/2006 | Rzasa et al. | 356/300 |
| 7,058,584 B2 | 6/2006 | Kosinski et al. | |
| 7,111,780 B2 | 9/2006 | Broussard et al. | |
| 7,139,639 B2 | 11/2006 | Broussard et al. | |
| 7,171,992 B2 | 2/2007 | DiGianfilippo et al. | |
| 7,769,601 B1 | 8/2010 | Bleser et al. | |
| 7,796,799 B2 * | 9/2010 | Jorritsma | 382/141 |
| 2001/0009005 A1 | 7/2001 | Godin et al. | |
| 2002/0019786 A1 | 2/2002 | Gonzalez et al. | |
| 2002/0052770 A1 | 5/2002 | Podrazhansky | |
| 2002/0062175 A1 | 5/2002 | Lion | |
| 2002/0062230 A1 | 5/2002 | Morag et al. | |
| 2002/0120573 A1 | 8/2002 | McCormick | |
| 2002/0147617 A1 * | 10/2002 | Schoenbaum et al. | 705/4 |
| 2002/0153411 A1 * | 10/2002 | Wan et al. | 235/375 |
| 2002/0188467 A1 | 12/2002 | Eke | |
| 2002/0198454 A1 | 12/2002 | Seward et al. | |
| 2003/0074234 A1 | 4/2003 | Stasny | |
| 2003/0109950 A1 | 6/2003 | Andrade et al. | |
| 2003/0135388 A1 * | 7/2003 | Martucci et al. | 705/2 |
| 2003/0149599 A1 | 8/2003 | Goodall et al. | |
| 2003/0179287 A1 * | 9/2003 | Kozic et al. | 348/14.08 |
| 2003/0225595 A1 * | 12/2003 | Helmus et al. | 705/2 |
| 2004/0019794 A1 | 1/2004 | Moradi et al. | |
| 2004/0117046 A1 | 6/2004 | Colle et al. | |
| 2004/0128162 A1 * | 7/2004 | Schlotterbeck et al. | 705/2 |
| 2004/0133705 A1 | 7/2004 | Broussard et al. | |
| 2004/0164146 A1 * | 8/2004 | Rosenblum | 235/381 |
| 2004/0172289 A1 * | 9/2004 | Kozic et al. | 705/2 |
| 2004/0220829 A1 | 11/2004 | Baharav et al. | |
| 2004/0221034 A1 | 11/2004 | Kausik et al. | |
| 2004/0260577 A1 | 12/2004 | Dahlin et al. | |
| 2005/0075902 A1 | 4/2005 | Wager et al. | |
| 2005/0125798 A1 | 6/2005 | Peterson | |
| 2006/0041330 A1 | 2/2006 | Ansari et al. | |
| 2006/0253346 A1 * | 11/2006 | Gomez | 705/28 |
| 2006/0276933 A1 | 12/2006 | Chavez et al. | |
| 2006/0287906 A1 | 12/2006 | McGillin | |
| 2007/0088565 A1 | 4/2007 | Berkelhamer et al. | |
| 2007/0088566 A1 | 4/2007 | Berkelhamer et al. | |
| 2007/0088567 A1 | 4/2007 | Berkelhamer et al. | |
| 2007/0088568 A1 | 4/2007 | Goodall et al. | |
| 2007/0088569 A1 | 4/2007 | Berkelhamer et al. | |
| 2007/0088590 A1 | 4/2007 | Berkelhamer et al. | |
| 2007/0088594 A1 | 4/2007 | Goodall et al. | |
| 2007/0088596 A1 | 4/2007 | Berkelhamer et al. | |
| 2007/0214014 A1 * | 9/2007 | Suwalski et al. | 705/3 |
| 2008/0119958 A1 * | 5/2008 | Bear et al. | 700/244 |
| 2008/0306761 A1 | 12/2008 | George et al. | |

OTHER PUBLICATIONS

McNaughton, "Can Net Drugstores Outpace the Chains?" CNET News.com, Feb. 24, 1999, 1 page.

Walgreens On-line Prefills (Website Printout Packet-printed Jul. 5, 2006) archived as Jun. 17, 1998, p. 1-13.

Wolverton, "Online Pharmacies Partner for Power," CNET News.com, Oct. 8, 1999, pp. 1-2.

"File Locking," www.wikipedia.org/wili/file_locking obtained via web.archive.com.

"Optimize your Enterprise for Maximum Profitability," NDCHEALTH, May 5, 2005, 4 pages.

Jones MJ, Internet-based Prescription of Sildenafil: A 2104-Patient Series, J. Med Internet Res 2001: 3(1): e2, http://www.jmir.org/2001/1/e2.

Office Action dated Mar. 29, 2004, U.S. Appl. No. 10/104,615, 10 pages.

Final Office Action dated Sep. 15, 2004, U.S. Appl. No. 10/104,615, 13 pages.

Office Action dated Nov. 1, 2006, U.S. Appl. No. 10/104,615, 6 pages.

Office Action dated Jul. 17, 2007, U.S. Appl. No. 10/104,615, 6 pages.

Office Action dated May 2, 2008, U.S. Appl. No. 10/104,615, 6 pages.

Final Office Action dated Feb. 3, 2009, U.S. Appl. No. 10/104,615, 8 pages.

Office Action dated Aug. 19, 2009, U.S. Appl. No. 10/104,615, 8 pages.

Final Office Action dated May 13, 2010, U.S. Appl. No. 10/104,615, 10 pages.

Appeal papers, U.S. Appl. No. 10/104,615, 104 pages.

Office Action dated Aug. 22, 2007, U.S. Appl. No. 10/376,177, 14 pages.

Final Office Action dated Apr. 30, 2008, U.S. Appl. No. 10/376,177, 14 pages.

Office Action dated Dec. 8, 2008, U.S. Appl. No. 10/376,177, 20 pages.

Final Office Action dated Oct. 14, 2009, U.S. Appl. No. 10/376,177, 13 pages.

Office Action dated Jun. 22, 2010, U.S. Appl. No. 10/376,177, 18 pages.

Application filed Sep. 28, 2007, U.S. Appl. No. 11/863,953, to Wiener, 30 pages.

Office Action dated Aug. 10, 2010, U.S. Appl. No. 11/863,953, 18 pages.

Office Action dated Apr. 1, 2010, U.S. Appl. No. 11/795,534, 15 pages.

* cited by examiner

SYSTEM AND METHOD FOR PERFORMING A REMOTE VERIFICATION OF A PHARMACY FILL UTILIZING AN IMAGE TO IMAGE COMPARISON

FIELD OF THE INVENTION

The present invention generally relates to a process for remote verification of a physical product corresponding to a product work order.

BACKGROUND

Existing retail networks performing order processing may suffer from inefficient distribution of workload. Many factors may contribute to this inefficient distribution across a network. One source of inefficiency may be the inability to redirect a portion of a work order process from a first pharmacy resource that lacks capacity to process that portion of the work order to a location in which there is additional capacity to process that type of work. This inability to distribute the particular work portion or work type may be due to an inability to dissociate the work portion from a physical aspect of the work order. For example, while some portions of a work order filling process, such as information processing, may be distributed remotely, some portions may currently require product specific or location specific handling that does not allow the portion of work to be easily reallocated away from a product location, thereby underutilizing available resources at network locations away from the product.

In a pharmacy application, an order process aspect that has traditionally required onsite handling of a specific pharmacy product is product verification. Not only may the pharmacist need to be onsite, some systems may require that the pharmacist be in proximity of the pharmacy product for the prescription order to be verified. The verification process may be further complicated if a specialist is required to perform the product verification. For example, while a non-pharmacist technician may assist in preparing a drug prescription (for example, by filing a vial with a certain amount of a drug) a registered pharmacist, may still be required to inspect and sign off on the pharmacy product. Thus, existing prescription order processing systems may be dependent on the availability of a specialist at a particular location.

SUMMARY OF THE INVENTION

The method and system provides image data from a first location to a second location and enables a product verification process to be performed by a user remote from the location of a physical product undergoing the verification process. The method and system enables the verification process to be ported to locations in which resources may be more efficiently utilized. Separation of an information processing portion of the verification process from the overall product filling process may allow the order filling process to be more easily divided and distributed to one of a plurality of organizational units within a network. In a pharmacy situation, the verification process may be distributed among a plurality of pharmacy resources that are connected by a computer network by distributing the image data accordingly. While the specific method and system will be described to apply to a pharmacy retail network embodiment, it is emphasized that this process may be applied to other retail industries as well.

In one embodiment, to further ensure the integrity of an order filling process, such as a drug prescription filling process, original order data, which may take the form of an unprocessed, scanned-in prescription image, may be used in the verification process.

DETAILED DESCRIPTION

Although the following text sets forth a detailed description of numerous different embodiments, it should be understood that the legal scope of the invention is defined by the words of the claims set forth at the end of this patent. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '______' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
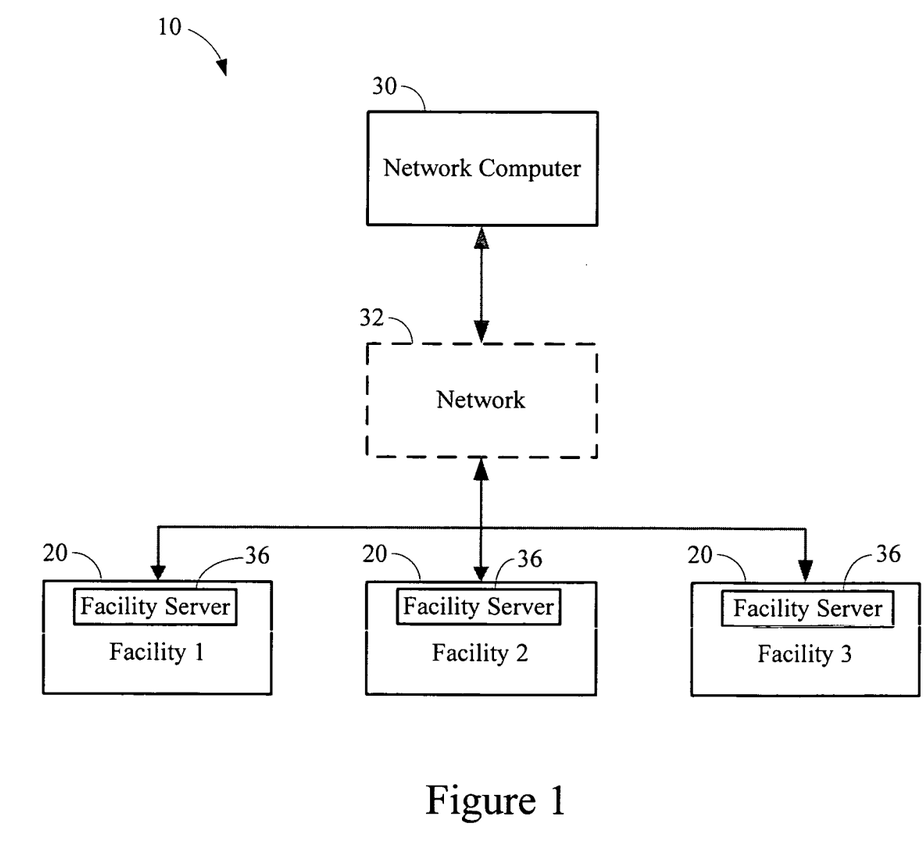
FIGS. 1-3 illustrate block diagrams of a computing system that may operate in accordance with the described embodiments.

FIG. 1 illustrates an embodiment of a data network 10 including a first group of pharmacies 20 operatively coupled to a network computer 30 via a network 32. The plurality of pharmacies 20 may be located, by way of example rather than limitation, in separate geographic locations from each other, in different areas of the same city, or in different states. The network 32 may be provided using a wide variety of techniques well known to those skilled in the art for the transfer of electronic data. For example, the network 32 may comprise dedicated access lines, plain ordinary telephone lines, satellite links, combinations of these, etc. Additionally, the network 32 may include a plurality of network computers or server computers (not shown), each of which may be operatively interconnected in a known manner. Where the network 32 comprises the Internet, data communication may take place over the network 32 via an Internet communication protocol.

The network computer 30 may be a server computer of the type commonly employed in networking solutions. The network computer 30 may be used to accumulate, analyze, and download pharmacy data. For example, the network computer 30 may periodically receive data from each of the pharmacies 20 indicative of information pertaining to a prescription order, billing information, employee data, etc. The pharmacies 20 may include one or more facility servers 36 that may be utilized to store information for a plurality of customers/employees/accounts/etc. associated with each facility.

Although the data network 10 is shown to include one network computer 30 and three pharmacies 20, it should be understood that different numbers of computers and pharmacies may be utilized. For example, the network 32 may include a plurality of network computers 30 and dozens of pharmacies 20, all of which may be interconnected via the network 32. According to the disclosed example, this configuration may provide several advantages, such as, for example, enabling near real time uploads and downloads of information as well as periodic uploads and downloads of information. This provides for a primary backup of all the information generated in the process of updating and accumulating pharmacy data.

Figure 2:
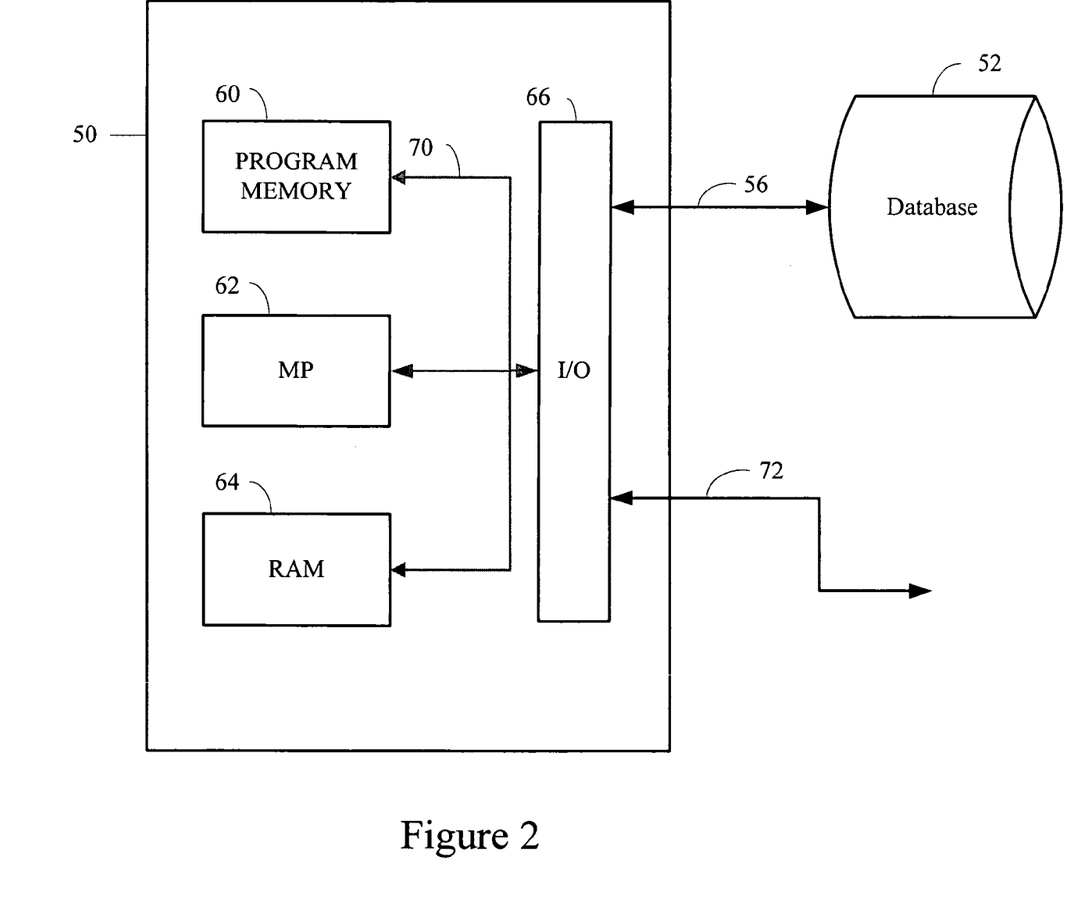

FIG. 2 is a schematic diagram of one possible embodiment of the network computer 30 shown in FIG. 1. The network computer 30 may have a controller 50 that is operatively connected to a database 52 via a link 56. It should be noted that, while not shown, additional databases may be linked to the controller 50 in a known manner.

The controller 50 may include a program memory 60, a microcontroller or a microprocessor (MP) 62, a random-access memory (RAM) 64, and an input/output (I/O) circuit 66, all of which may be interconnected via an address/data bus 70. It should be appreciated that although only one microprocessor 62 is shown, the controller 50 may include multiple microprocessors 62. Similarly, the memory of the controller 50 may include multiple RAMs 64 and multiple program memories 60. Although the I/O circuit 66 is shown as a single block, it should be appreciated that the I/O circuit 66 may include a number of different types of I/O circuits. The RAM(s) 64 and programs memories 60 may be implemented as semiconductor memories, magnetically readable memories, and/or optically readable memories, for example. The controller 50 may also be operatively connected to the network 32 via a link 72.

Figure 3:
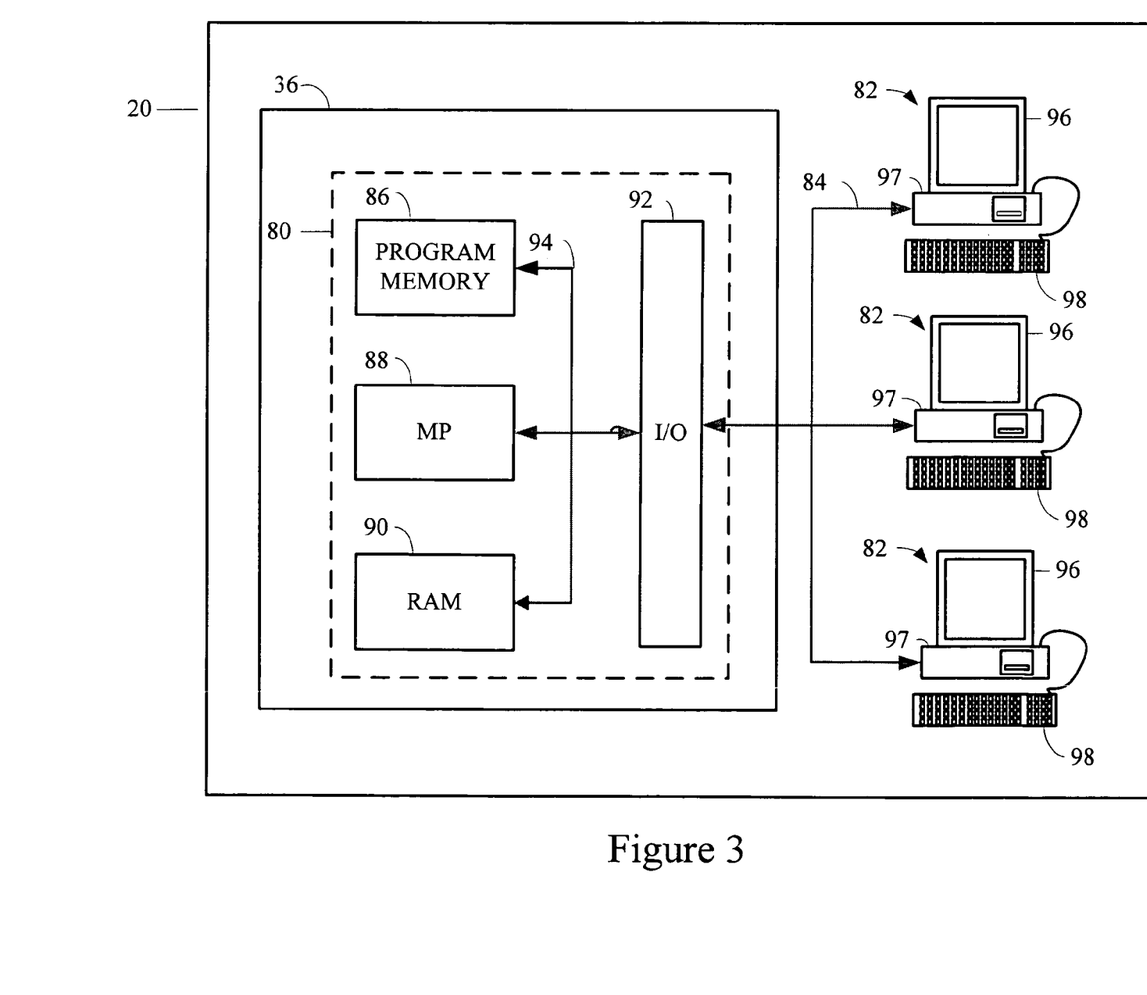

FIG. 3 is a schematic diagram of one possible embodiment of several components located in one or more of the pharmacies 20 from FIG. 1. Although the following description addresses the design of the pharmacies 20, it should be understood that the design of one or more of the pharmacies 20 may be different than the design of other pharmacies 20. Also, each pharmacy 20 may have various different structures and methods of operation. It should also be understood that the embodiment shown in FIG. 3 illustrates some of the components and data connections present in a pharmacy, however it does not illustrate all of the data connections present in a typical pharmacy. For exemplary purposes, one design of a pharmacy is described below, but it should be understood that numerous other designs may be utilized.

The pharmacies 20 may have a facility server 36, which includes a controller 80, wherein the facility server 36 is operatively connected to a plurality of client device terminals 82 via a network 84. The network 84 may be a wide area network (WAN), a local area network (LAN), or any other type of network readily known to those persons skilled in the art. The client device terminals 82 may also be operatively connected to the network computer 30 from FIG. 1 via the network 32.

Similar to the controller 50 from FIG. 2, the controller 80 may include a program memory 86, a microcontroller or a microprocessor (MP) 88, a random-access memory (RAM) 90, and an input/output (I/O) circuit 92, all of which may be interconnected via an address/data bus 94. As discussed with reference to the controller 50, it should be appreciated that although only one microprocessor 88 is shown, the controller 80 may include multiple microprocessors 88. Similarly, the memory of the controller 80 may include multiple RAMs 90 and multiple programs memories 86. Although the I/O circuit 92 is shown as a single block, the I/O circuit 92 may include a number of different types of I/O circuits. The RAM(s) 90 and programs memories 86 may also be implemented as semiconductor memories, magnetically readable memories, and/or optically readable memories, for example.

The client device terminals 82 may include a display 96, a controller 97, a keyboard 98 as well as a variety of other input/output devices (not shown) such as a scanner, printer, mouse, touch screen, track pad, track ball, isopoint, voice recognition system, digital camera, etc. Each client device terminal 82 may be signed onto and occupied by a pharmacy employee to assist them in performing their duties. Pharmacy employees may sign onto a client device terminal 82 using any generically available technique, such as entering a user name and password. If a pharmacy employee is required to sign onto a client device terminal 82, this information may be passed via the link 84 to the facility server 36, so that the controller 80 will be able to identify which pharmacy employees are signed onto the system and which client device terminals 82 the employees are signed onto. This may be useful in monitoring the pharmacy employees' productivity.

Typically, facility servers 36 store a plurality of files, programs, and other data for use by the client device terminals 82 and the network computer 30. One facility server 36 may handle requests for data from a large number of client device terminals 82. Accordingly, each facility server 36 may typically comprise a high end computer with a large storage capacity, one or more fast microprocessors, and one or more high speed network connections. Conversely, relative to a typical facility server 36, each client device terminal 82 may typically include less storage capacity, a single microprocessor, and a single network connection.

Figure 4:
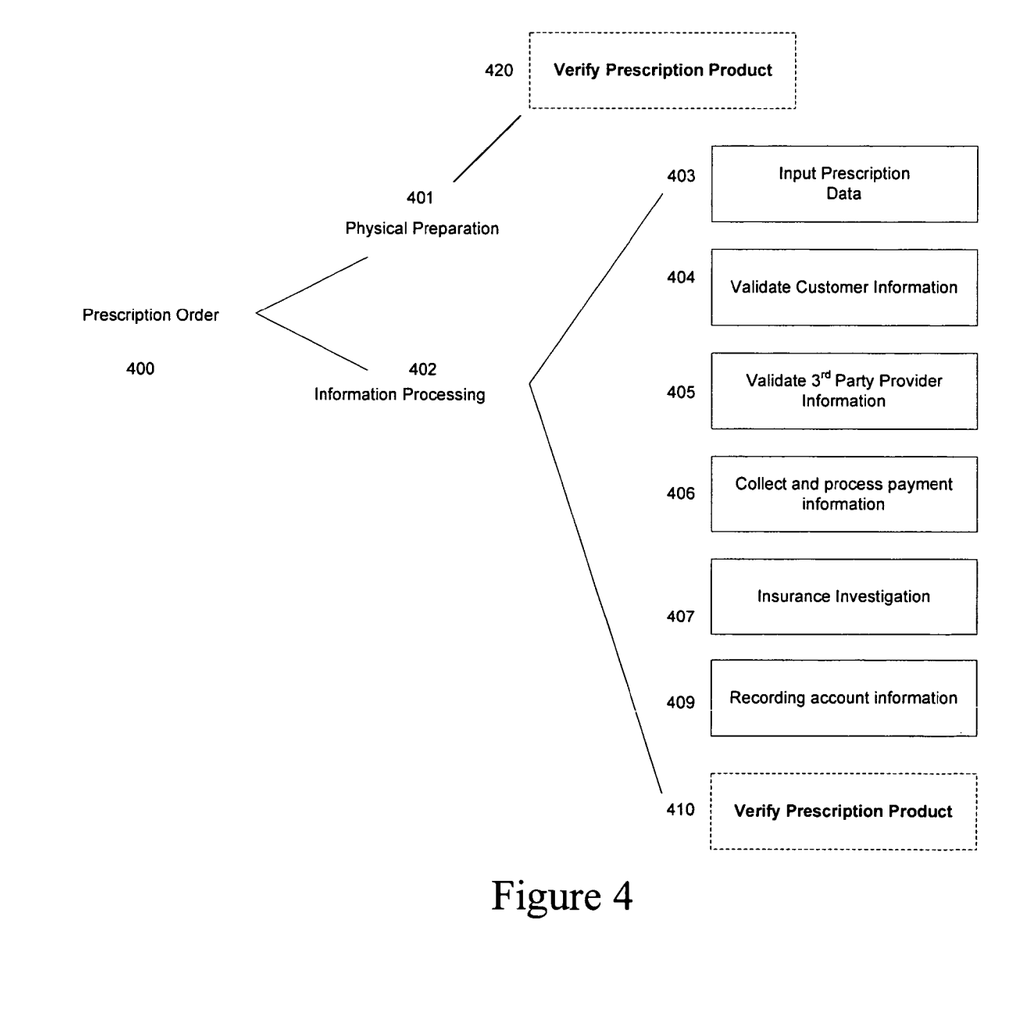
FIG. 4 illustrates types of work involved in a prescription order filling process.

Processing of a work order for a physical product may involve physical processing steps and information processing steps. For example, FIG. 4 illustrates that processing of a pharmacy prescription drug order 400 may be separated into physical processing of the order 401 and information processing of the order 402. Information processing 402 may include entering the original prescription order data into a system 403 as well as all the steps that need to be performed to the order data contemporaneously with physical preparation of the pharmacy product 401. Some of the information processing steps may include work related to inputting prescription data 403, validating customer information 404, validating third-party provider information 405, collecting payment information 406, investigating insurance 407, and recording accounting information into an accounting database 409.

Figure 5:
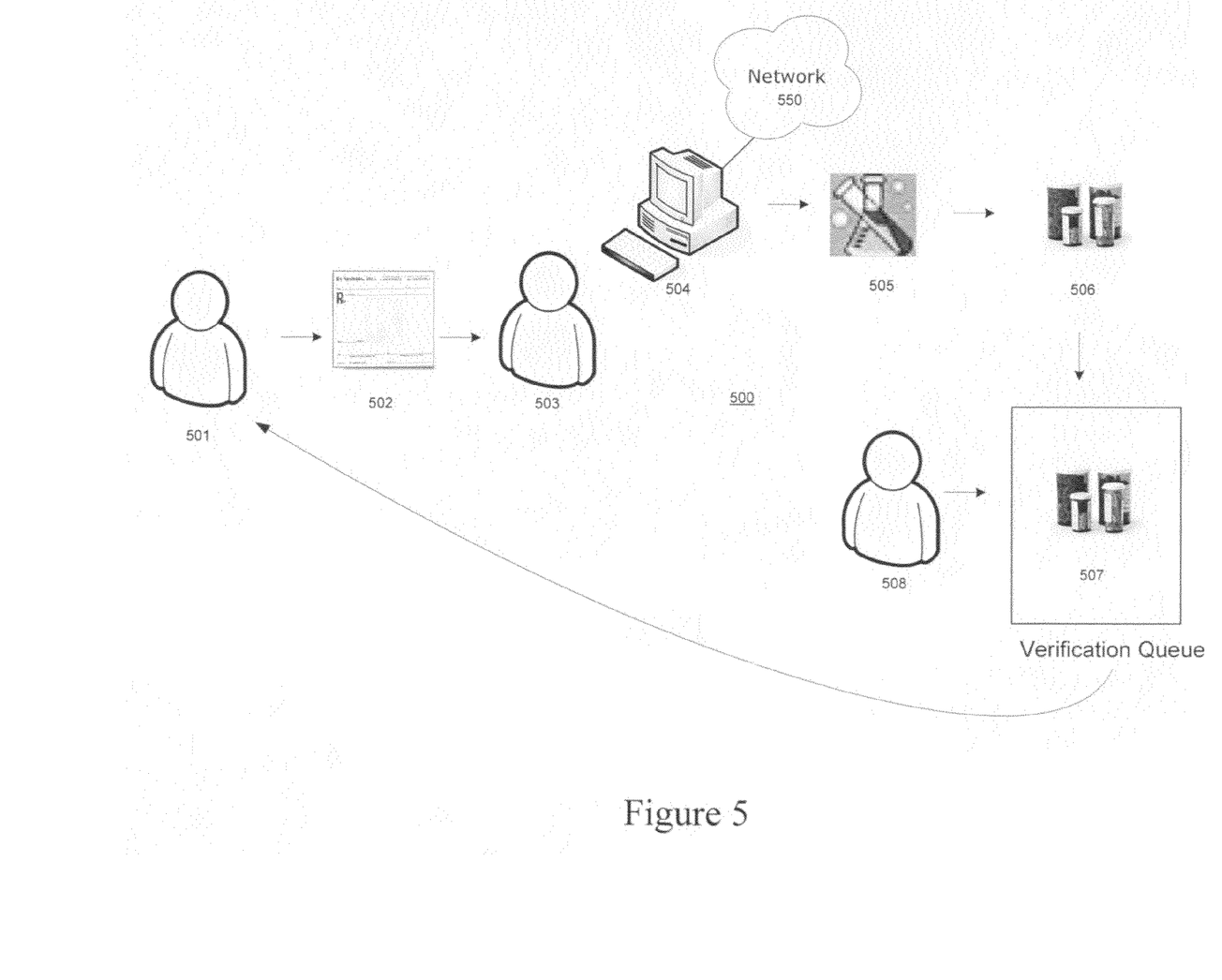
FIG. 5 illustrates a general prescription order filling process.

FIG. 5 illustrates a general prescription order filling process. A first pharmacy resource 500 may include, for example, a pharmacist, a technician or non-pharmacist assistant 503 that receives a physical prescription 502 from a customer 501 and inputs the prescription order 502 into a networked computer 504. Some of the information processing 402 illustrated in FIG. 4 may be distributed to other technicians, pharmacists, or assistants onsite or remotely (via network 550) for processing. A pharmacist or technician may contemporaneously begin physical preparation of the pharmacy product for the prescription order 505. After the physical pharmacy product is prepared 506, but before the product is delivered to a customer 501, the pharmacy product 506 may be placed in a physical verification queue 507 or storage container. The pre-verification product orders in the verification queue 507 may await a registered pharmacist to perform verification. After a verification process by a registered pharmacist 508, the pharmacy product may be approved for delivery to the customer 501 that placed the order. If the pharmacy product is discovered to be deficient or defective in any way during the verification process, then the prescription order may be discarded and a new prescription order may be processed. If the deficiency can be easily remedied, for example, when there are too few units in the prescription order (an amount of product may also be a product characteristic), then a new prescription order may be unnecessary. Instead, if the deficiency can be easily remedied, the pharmacy product may be held at the verification queue 507 until the deficiency is remedied and a second verification process approves the product.

Product verification may generally involve determining whether the pharmacy product actually prepared corresponds to the pharmacy product ordered via a prescription order. This may involve determining the identity of the product in the pre-verification queue and comparing the pre-verification product to reference information of the product on the prescription order. For example, the prescription order may contain drug identifying information such as a drug name, a drug type, and/or other drug characteristics. The drug identifying information may include a drug identifier such as a drug code that may identify the drug in a reference source (e.g., a physical index or database). The drug identifying information may be used to retrieve reference information on the pharmacy product for comparison against the prepared product. Product verification may also be based on a pharmacist's own knowledge of drug information. For example, the pharmacist may recognize the drug identifier or other drug identifying information and based on the pharmacist's knowledge of a characteristic of the prescription order product, examine the prepared product to determine if it corresponds to the product identified in the prescription order.

In existing processes, verification of a pharmacy product order may require onsite handling of a physical pharmacy product because a pharmacist may need to view the physical product to obtain image information. Thus, verification may be regarded as a physical process 420 (see FIG. 4) that may not be easily distributed. Further complicating distribution of verification work is that verification may need to be performed by a specialist, such as a registered pharmacist. However, verification may also involve an information processing portion 410 (see FIG. 4). For example, the pharmacist must analyze information pertaining to a physical characteristic of a product (e.g., appearance) and determine whether that physical characteristic corresponds to a characteristic of the product ordered by a customer. Thus, while acquisition of the physical characteristics of a product may primarily be a physical process, analytical processing of the physical characteristic may be an information processing step that may be dissociable from the physical product and location of the physical product. Furthermore, it is the analysis of the physical characteristic of the prepared pharmacy product against information of the characteristic of a pharmacy product designated in a prescription order that must be performed by a pharmacist (not necessarily the acquisition of pharmacy product characteristics).

Figure 6:
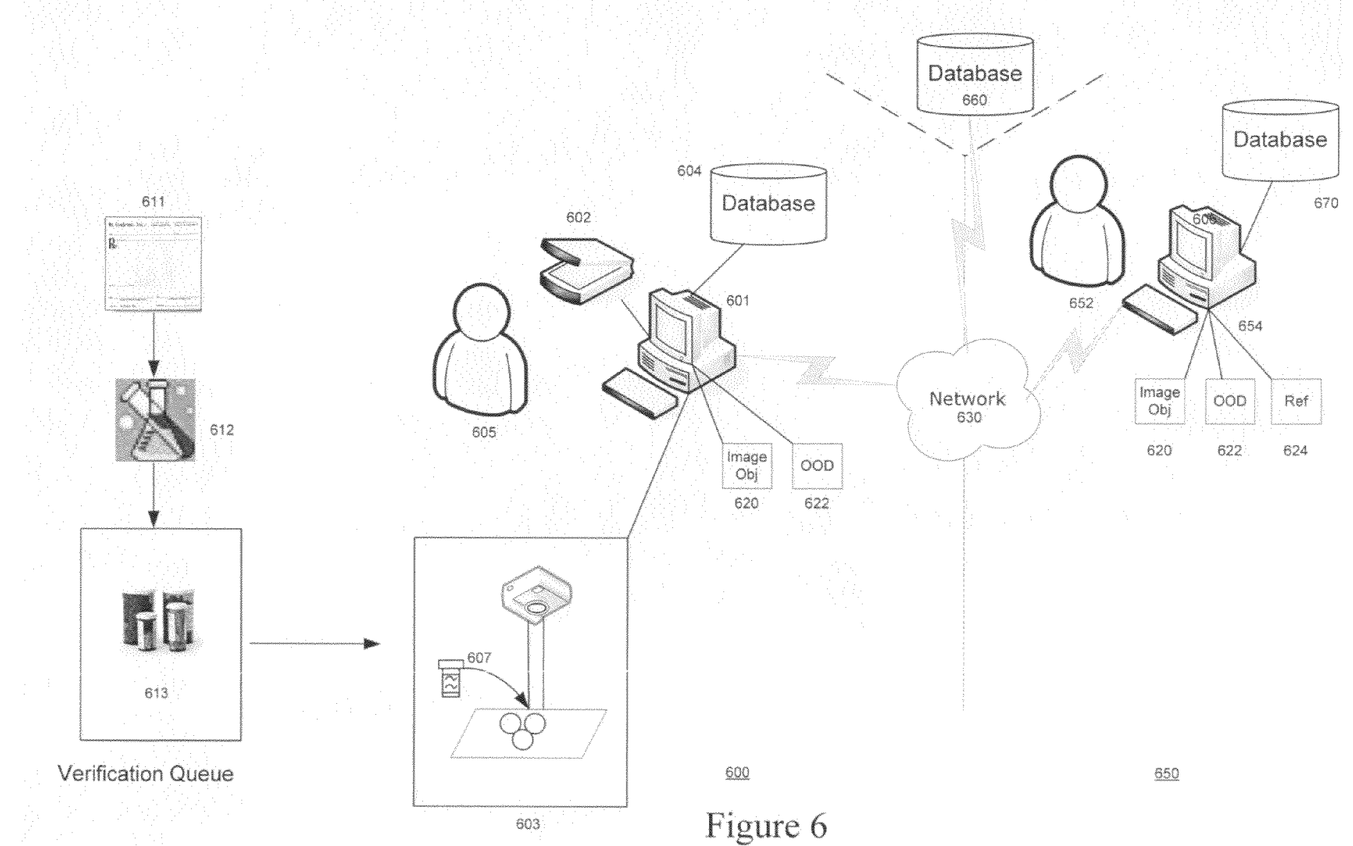
FIG. 6 illustrates a system embodiment for enabling remote verification of a product order.

To enable geographic separation of verification work in which different entities and geographically separated personnel perform verification for a prescription order, the pharmacy information system and method may acquire image data of a prepared pharmacy product for a remote pharmacist to analyze. FIG. 6 illustrates a system embodiment for enabling remote verification of a product order, such as a prescription drug order. A first pharmacy resource 600 at a first location may include a first computer 601 that is connected to a pharmacy computer network 630. The computer 601 may be connected to a document scanner 602 and a digital camera or other digital imaging device/system 603. While FIG. 6 illustrates that the scanner and camera are two separate devices, it should be noted that a scanner and camera could be combined into a single device providing both functions. Moreover, while the devices are illustrated as being connected to a separate workstation (which is then connected to network 630), it should be noted that these devices may be independently networked enabled devices that are capable for connecting directly to network 630.

The document scanner 602 may be used to scan customer specific data such as insurance information, payment information, etc. The document scanner 602 may also capture original order data, such as an image of a physical prescription 611, and create an original order data object 622. The digital imaging device 603 may be used to scan a sample of a physical product 607 that is associated with a prescription order 611. This image data may form an image data object 620. In one embodiment, a local pharmacist or technician 605 may operate the computer 601, scanner 602, and/or camera 603 to capture data. Alternatively, this data capture process may be automated.

In one embodiment, the sample may be taken from a prepared pharmacy product (produced via a physical preparation process 612) in a pre-verification queue 613. The image data object 620 may then be stored on a local database 604 or a central database 660. The image data object 620 may then be associated with an electronic prescription order on the pharmacy network 630. This electronic prescription order may include all the information from the physical prescription information. An original order data object 622 formed from scanning the physical prescription into the network system may be associated with the electronic prescription order.

In one embodiment, the verification queue or storage container may represent a delivery bin containing both verified and non-verified filled product/prescription orders. In this embodiment, when a customer requests his order for pickup, a pharmacist, technician or non-pharmacist, may retrieve first the customer's product order from the bin. Before delivering the order to the customer, however, the pharmacist, technician or non-pharmacist, must scan the order in to a register computer. The register computer may then access a database connected to the network to determine whether or not the product order is verified. If it is not verified, the register computer may be programmed to automatically block the sale or delivery of the product to the customer.

A remote pharmacist 652 located at second pharmacy resource 650 having a second computer 654 may then perform verification of the pharmacy product for the prescription order. The remote pharmacist 652 may use the second computer 654 to retrieve the image data object 620 and display an image of the sample product 607 taken from a pre-verified prescription order product. The remote pharmacist 652 may then reference information in the electronic prescription order to determined the identity of a customer requested product. Once the remote pharmacist inspects the image data and determines that it corresponds (e.g., within a threshold) to the prescription order information, the remote pharmacist may provide an indication that the product is ready for release to a customer. If the product is deficient or defective, then the remote pharmacist 652 may raise an exception to the prescription order and provide an indication of the exception.

In one embodiment, the pharmacist 652 may be located in the same pharmacy resource 600 to perform the verification described above. In this embodiment, any computer connected to the network 630 (including 601) may be used to verify a prepared pharmacy product, including additional computers at the same pharmacy location. It should be noted that the image data allows a pharmacist to perform verification without viewing the actual prepared drug. Thus, a pharmacist may perform verification from a back room, away from the area of the pharmacy 603 where a pharmacy product is prepared and/or stored.

Figure 7:
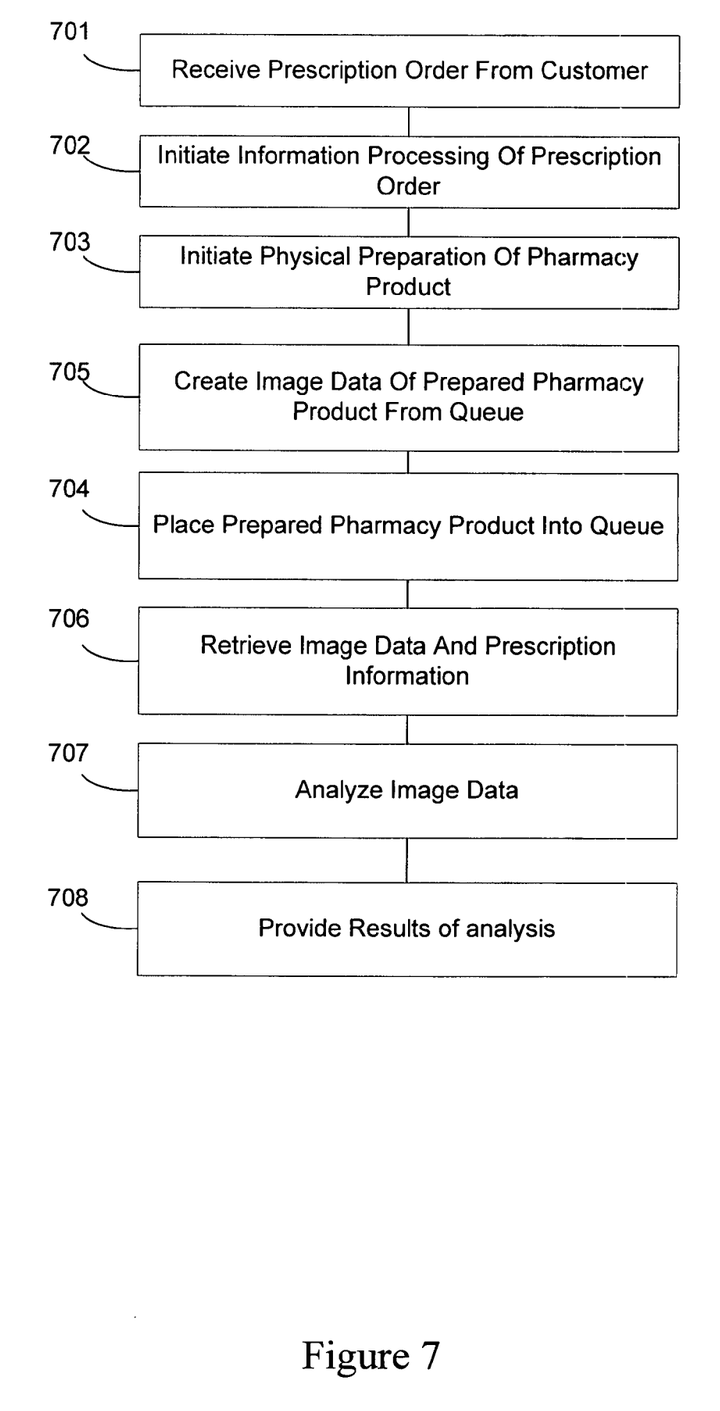
FIG. 7 illustrates a general process embodiment of the claimed system.

FIG. 7 illustrates a general process embodiment of the claimed system. In this embodiment, any pharmacy worker (e.g., pharmacist, technician, assistant) may receive a prescription order from a customer 701, and initiate information processing of the prescription order 702. Information processing may include entering data for the prescription order. This data entry may be performed by a technician. To ensure accuracy of the data and to provide safety for customers, a pharmacist may perform a review of the entered prescription before any further processing steps are taken. This may involve reviewing the entered data against the actual prescription order (or an electronic copy of the prescription order). This may also involve reviewing the ordered product against past prescriptions and other customer or patient medical data that is available to the pharmacist. This review may involve detecting or checking for any possible adverse reactions based on medical conditions of the customer or patient. The review may include, for example, checking that the dosage is correct for the physical characteristics of the patient. For example, the dosage may be checked to ensure that it is appropriate for a child (versus adult concentrations). The review may also check for possible allergic reactions to drugs based on past prescription history and medical data.

After information processing and data review, physical preparation of the pharmacy product 703 may be initiated. It should be noted that portions of information processing may be performed contemporaneously with a portion of the information processing. Physical preparation of the pharmacy product may include using a scale or other measuring device to measure a quantity of the pharmacy product for filling the prescription. A pharmacy worker may then acquire image data of the pharmacy product to create an image data object of the pharmacy product 704. In one embodiment, the image data may be captured at the time the pharmacy product is being measured. In another embodiment, the image data may be captured at a later time (e.g., after the pharmacy product is placed in a container).

Once the pharmacy product associated with a prescription order is prepared, the product may be placed in a verification queue 705 and await verification. A pharmacist may then retrieve the image data along with prescription order information 706 and perform an analysis on the image data using the prescription order data 707. It should be noted that the pharmacist retrieving the image data 706 and performing the review 707 may be located in a different pharmacy location or the same pharmacy location that captured the image data of the prepared pharmacy product. Using the system and method described herein, the pharmacist does not need to physically view or be able to view the dispensed/prepared pharmacy product to perform analysis. Even when the pharmacist is located in the same pharmacy location with the prepared product, this system enables the pharmacist to conveniently retrieve the necessary images and other data to perform verification analysis without having to handle the actual prepared product and without having to have the prepared product brought for viewing. After the analysis is performed, the results of the analysis may be provided 708.

Analyzing image data 707 may involve an experienced pharmacist referencing personal knowledge about a pharmacy product based on the prescription information and analyzing the image data based on this personal knowledge. The remote computer may also run an image comparison program that provides an analysis of two pharmacy product images. The image comparison program may match shape, size, and color of the pharmacy products to determine a correlation. In one embodiment, the image comparison program may provide a first estimate of the likelihood that the two products match and await input from the remote pharmacist before indicating approval of the product for delivery to a customer.

Figure 8:
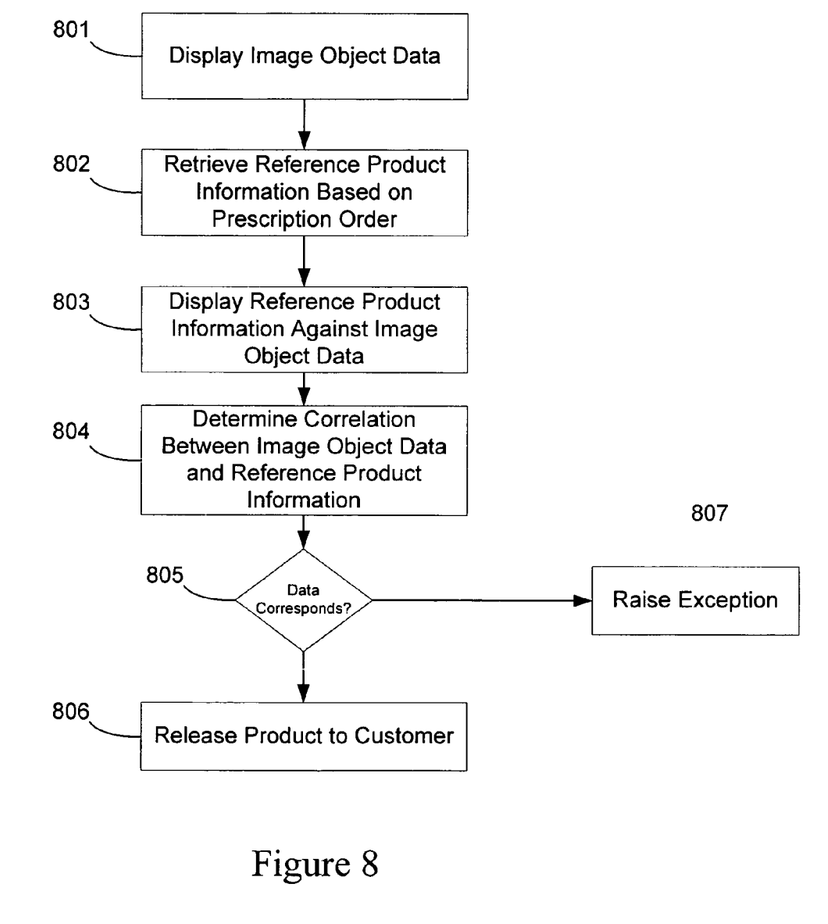
FIG. 8 illustrates an embodiment of a verification analysis process.

FIG. 8 illustrates an embodiment of a verification analysis process. A pharmacist at a remote location may retrieve the image object and display it on a remote computer screen 801. The pharmacist may then reference a database 604, 660, or 670 to retrieve drug and/or product characteristic information 802. The reference information, which may be in the form of a reference object 624, may provide descriptions of the physical appearance of a drug or pharmacy product which the pharmacist may then use to determine the identity of the product or the quality of the product. The reference data may contain image objects of drug and other pharmacy products that may be used in the analysis of the image data for the pre-verification product.

In one embodiment, the reference image objects may be indexed by a drug identifier. The drug identifier may be a drug name, a drug type, a drug reference number etc. A drug identifier may be provided as part of a customer prescription order. The drug identifier may be captured when the electronic prescription order is formed. When a pharmacist at the second computer 654 initiates a verification process for a product 607, the pharmacist may use the second computer 654 to retrieve a reference image object 624 or other product reference data based on a drug identifier on the electronic prescription order.

Figure 9:
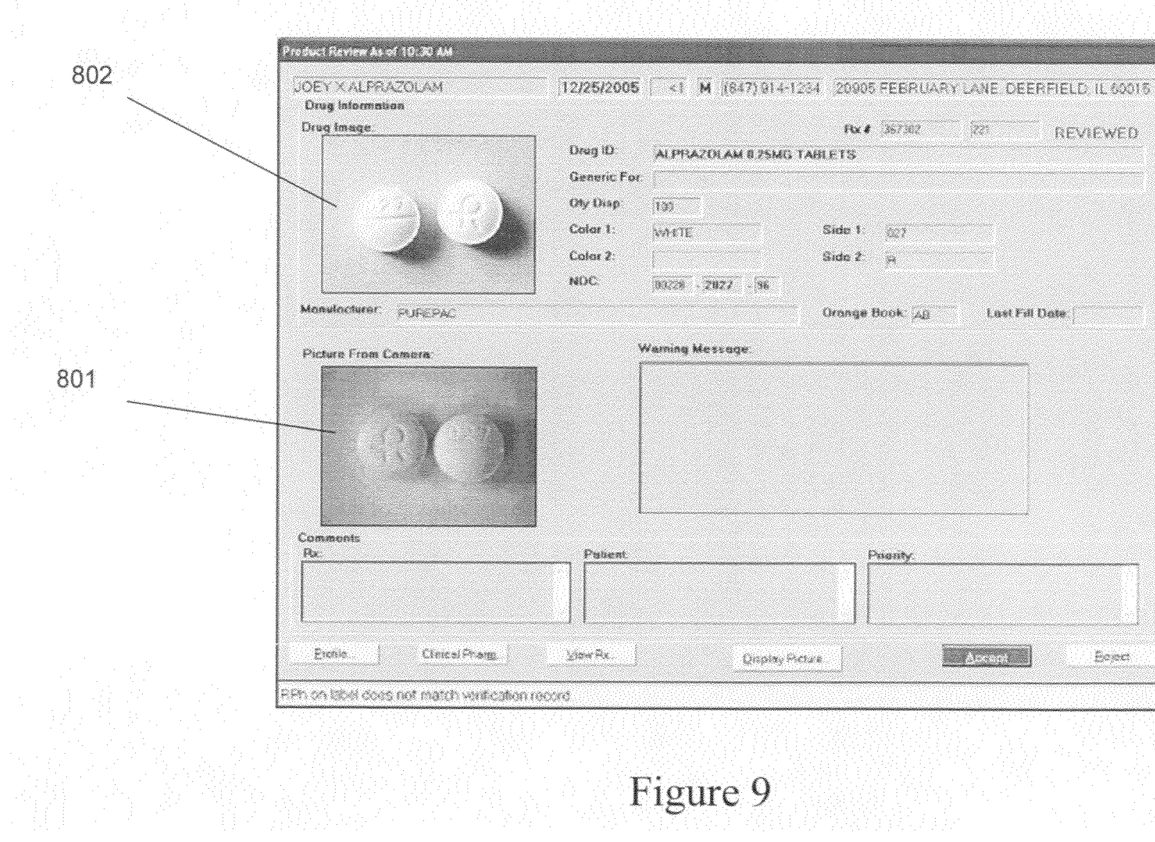
FIG. 9 illustrates an exemplary display tool embodiment.
Figure 10:
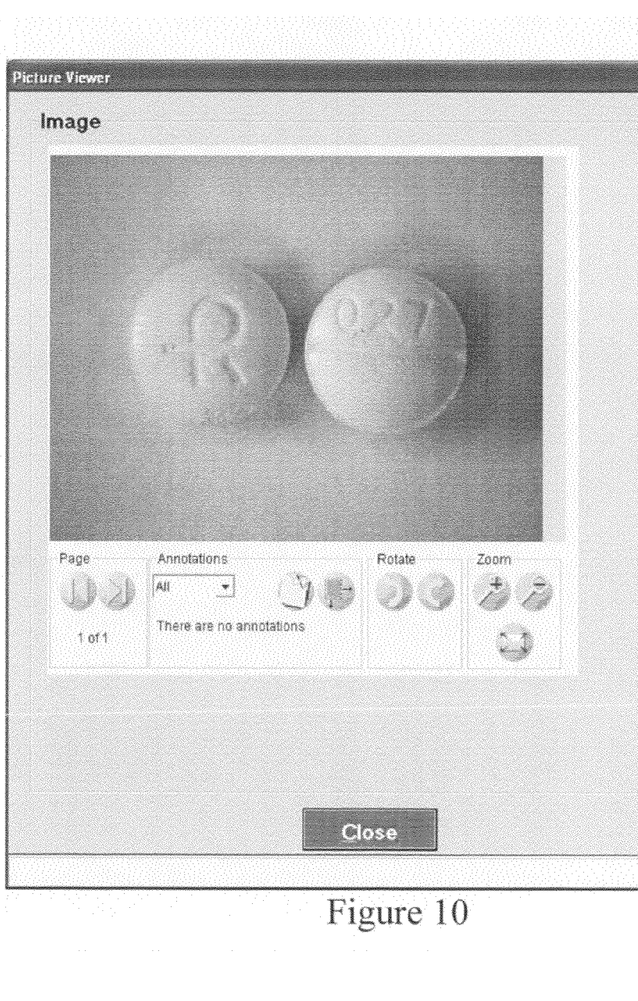
FIG. 10 illustrates an exemplary display tool embodiment providing a user the option to manipulate a captured image.

The remote computer 654 used by the remote pharmacist 652 for verification may be adapted to display an image of the prepared pharmacy product and a reference image of a pharmacy product corresponding to information from the electronic prescription 803. As illustrated in FIG. 9, an image of the prepared drug 901 and 903 may be displayed adjacent one another to facilitate easier comparison of image characteristics by the remote pharmacist. The remote computer 654 may be adapted to position the sample product image to correspond with an alignment of the reference image, or vice versa. For example, in a case in which the pharmacy product is a drug in pill form, the remote computer may crop the pills and align them so that their markings coincide with the angle of the pills shown on the reference image. This positioning may be automatic or may simply be provided as an option to the user of the second computer. FIG. 10 illustrates an exemplary screen providing a user the option to manipulate a captured image. The screen may be modified to crop the pills as well.

As illustrated in FIG. 8, the remote pharmacist 652 may determine the correlation between the image data of the prepared pharmacy product awaiting approval and reference product data 804. If the data corresponds within a certain degree or tolerance (or threshold) 805, then the pharmacy product may be approved for release and delivery to a customer 806. Otherwise, an exception may be raised 807.

Figure 11:
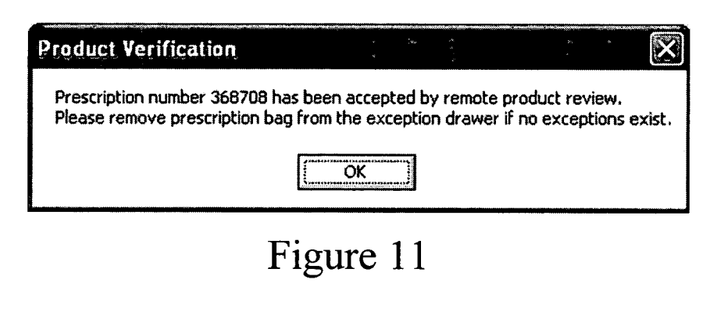
FIG. 11 illustrates an exemplary approval message indicator.
Figure 12:
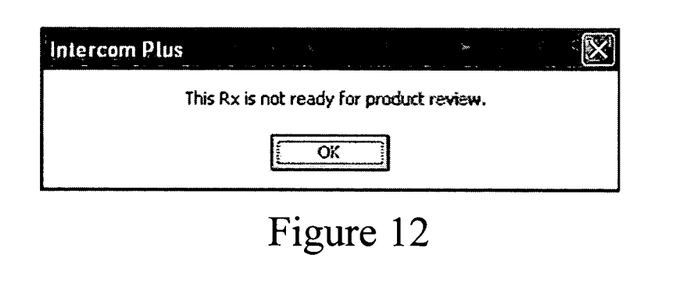
FIG. 12 illustrates an exemplary error message indicator.

The indication of the result of the verification process 708 (whether an approval or an error/exception) may be made by modifying an attribute on the electronic prescription order. In this case, when a user at the first pharmacy resource retrieves or looks up the status of the electronic prescription order, an indication of the exception may be displayed. Alternatively, the indication may be made by sending a message via a messaging system such as instant messaging, email, fax, etc. FIG. 11 illustrates a message that may be displayed at the first computer indicating approval. An exception may be raised if the image data is deficient. For example, the image data may be unreadable, or otherwise visually inadequate. This type of exception may prompt a worker at the first pharmacy resource to re-image the sample. The exception may also be raised if the product is on its face, not ready for inspection, as illustrated in FIG. 12.

In another embodiment, the pharmacist at the remote computer 654 may further verify appropriateness of the imaged sample product by referencing an original order data object 624 associated with the electronic prescription order. For example, the pharmacist may check a drug identifier or other pharmacy product identifier on the original order data object 624 (which could be an image of the actual physical prescription) to ensure that no data entry error exists in the electronic prescription order, and use the drug identifier of the original order data object to retrieve any reference information from the database. This step may help ensure that the drug sample under verification corresponds with the original prescription order, not just a drug identifier of the electronic prescription order which may be susceptible to input entry error.

The described method and system enables a product verification process to be performed remotely by a specialist or other worker. This enables the verification process to be ported to locations in which resources may be more efficiently utilized. For example, a pharmacy company having a plurality of pharmacy resources may redirect verification processing from a pharmacy resource having a low availability of verification pharmacists to a pharmacy resource having a high availability of verification pharmacists. The claimed system may also enable flexible pharmacy organization planning and allows for implementation of different workflows, e.g., different process order, for different types of work orders. The claimed system may also allow a pharmacy company to consolidate resources such as registered pharmacists. For example, a pharmacy company may find it economical to concentrate pharmacists and other specialists at a center to increase the speed of the verification process across the network. While the specific method and system will be described to apply to a pharmacy retail network embodiment, it is emphasized that this process may be applied to other retail network systems that require original order data to be referenced during the processing of a work order. Other network systems may include those for various technical products, legal document processing, and/or forensic processing.

What is claimed:

1. A method of verifying prescription drug orders within a network of pharmacy computers connected by an information processing system, the method comprising:

creating a first electronic image object of at least a sample of the physical drug product associated with the prescription order using a computerized imaging system connected to a first computer at a first pharmacy resource in a pharmacy;

directing verification processing of the prescription order from the first pharmacy resource in the pharmacy to a second pharmacy resource outside the pharmacy;

retrieving the first image object using a second computer at the second pharmacy resource, the second computer connected to the first computer via a computer network;

retrieving a reference image object of the physical drug product using the second computer;

determining at the second computer whether the physical drug product of the first image object associated with the prescription order corresponds to the physical drug product in the reference image object based on a comparison of the first image object and the reference image object without viewing the physical drug product associated with the prescription order, wherein determining whether the drug product of the first image object corresponds to the drug product of the reference image object includes:

(i) displaying a first image captured by the first image object adjacent a second image captured by the reference image object on a display of the second computer, wherein displaying the first image and the second image includes positioning one of the first image and the second image to align manufactured drug markings in the one of the first image and the second image with corresponding manufactured drug markings in the other of the first image and the second image, and (ii) visually comparing, by a user located at the second pharmacy resource using the second computer, comparing the visually aligned first image to the visually aligned second image; and releasing the drug prescription order at the pharmacy resource to a client after determining that the drug product of the first image object corresponds to the drug product of the reference image object.

2. The method of claim 1, further comprising automatically blocking the delivery of the drug product to a customer at a register computer before determining at the second computer whether the drug product of the first image object corresponds to the drug product of the reference image object.

3. The method of claim 1, wherein creating a first image object comprises taking a photo of a prescription drug and storing data associated with the photo in the first image object.

4. The method of claim 1, further comprising creating an index of image objects of drug products referenced by a drug identifier and wherein retrieving a reference image object corresponding to the first image object comprises retrieving an image object of a drug product from the index based on a drug identifier.

5. The method of claim 4, wherein the drug identifier is associated with a drug prescription order.

6. The method of claim 1, wherein displaying an indication that the first image object does not match the reference image object comprises displaying an indication at the first computer.

7. The method of claim 1, wherein the second computer is adapted to allow a user to raise the exception at the second computer.

8. The method of claim 1, further comprising capturing data on a drug prescription order from a customer corresponding to the drug product and determining whether there exists any adverse reactions to the drug product based on previous patient prescriptions and patient medical data.

9. The method of claim 1, further comprising raising an exception to a prescription order process when the drug product of the first image object does not correspond to the drug product of the reference image object, wherein raising an exception comprises one of associating an error flag with the first image object if the two image objects are dissimilar or displaying an indication that the first image object does not match the reference image object, and wherein the exception is one or more of an error indicating an unable-to-read situation or an error indicating that the drug product of the first image object does not correspond to the drug product of the reference image object.

10. The method of claim 1, wherein the manufactured drug markings in the one of the first image and the second image and the corresponding manufactured drug markings in the other of the first image and the second image include at least one of: (i) indicia representative of a drug product, (ii) a shape of a drug product, or (iii) a coloring of a drug product.

11. A system for enabling remote verification of a prescription order comprising:
 a first computer at a first pharmacy resource in a pharmacy;
 a measuring device to measure a quantity of a physical drug product for filling a prescription;
 an imaging system coupled to the first computer and adapted to create an image object of at least a sample of a physical drug product associated with a prescription order at the first pharmacy resource in the pharmacy during the time the physical drug product is being measured;
 wherein the first computer is adapted to direct the image object via a computer network from the first pharmacy resource to a second pharmacy resource with at least one available verification pharmacist outside the pharmacy and further adapted to display an indication of the result of a verification process based on a communication received by the first computer; and
 a second computer at the second pharmacy resource with at least one available verification pharmacist outside the pharmacy, the second computer connected to the first computer via a computer network,
 wherein the second computer is adapted to:
  retrieve the image object created at the first computer, to retrieve a reference image object corresponding to the physical drug product using the second computer,
  display the image object created at the first computer adjacent the reference image object on a display of the second computer, wherein displaying the first image and the second image includes positioning one of the first image and the second image to align manufactured drug markings in the one of the first image and the second image with corresponding manufactured drug markings in the other of the first image and the second image, and
  send a communication to the first computer as to whether the physical drug product of the first image object associated with the prescription order corresponds to the physical drug product in the reference image object based on a comparison of the first image object and the reference image object, wherein the communication to the first computer includes instructions to release the drug prescription order at the pharmacy resource to a client after determining that the drug product of the first image object corresponds to the drug product of the reference image object.

12. A method of verifying prescription drug orders within a network of pharmacy computers connected by an information processing system, the method comprising:
 receiving a prescription order from a customer by a pharmacy employee;
 entering prescription data based on the prescription order into a first computer at a first pharmacy resource in a pharmacy by the pharmacy employee;
 reviewing the entered prescription data by a verification pharmacist using a second computer at a second pharmacy resource with a different availability of verification pharmacists than at the pharmacy and located outside the pharmacy, the second computer connected to the first computer via a computer network;
 measuring a quantity of a physical drug product associated with the prescription order for filling the prescription order by the pharmacy employee;
 while the quantity of the physical drug product is being measured, creating a first electronic image of at least a sample of the physical drug product by the pharmacy employee using a computerized imaging system connected to either the first computer or a third computer in the pharmacy;
 directing verification processing of the physical product associated with the prescription order from the pharmacy to a second pharmacy resource with a different availability of verification pharmacists than at the pharmacy and located outside the pharmacy;
 retrieving the first electronic image using the second computer at the second pharmacy resource, the second computer connected to the first computer via a computer network by a verification pharmacist;
 retrieving an electronic reference image of the physical drug product using the second computer by the verification pharmacist; and
 determining by the verification pharmacist at the second computer, without the verification pharmacist viewing the physical drug product, whether the physical drug product of the first electronic image associated with the prescription order corresponds to the drug product in the electronic reference image based on a comparison of the first electronic image object and the electronic reference object, wherein determining whether the drug product of the first image object corresponds to the drug product of the reference image object includes:
  (i) displaying a first image captured by the first image object adjacent a second image captured by the reference image object on a display of the second computer, wherein displaying the first image and the second image includes positioning one of the first image and the second image to align manufactured drug markings in the one of the first image and the second image with corresponding manufactured drug markings in the other of the first image and the second image, and
  (ii) visually comparing, by a user located at the second pharmacy resource using the second computer, comparing the first image to the second image; and
 releasing the drug prescription order at the pharmacy resource to a client after determining that the drug product of the first image object corresponds to the drug product of the reference image object.

* * * * *